(12) United States Patent
Sacherer

(10) Patent No.: US 7,670,562 B2
(45) Date of Patent: Mar. 2, 2010

(54) DISPENSING CONTAINER AND STORAGE CONTAINER FOR ANALYTICAL DISPOSABLES

(75) Inventor: Klaus-Dieter Sacherer, Kirchheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1486 days.

(21) Appl. No.: 10/988,750

(22) Filed: Nov. 15, 2004

(65) Prior Publication Data

US 2005/0118071 A1 Jun. 2, 2005

(30) Foreign Application Priority Data

Nov. 15, 2003 (DE) ................. 103 53 445

(51) Int. Cl.
*B01L 3/00* (2006.01)
(52) U.S. Cl. .................. 422/102; 422/99; 422/100; 422/64; 422/63; 422/50
(58) Field of Classification Search ................. 422/102, 422/64, 50, 99, 63, 100; 206/449
See application file for complete search history.

(56) References Cited

U.S. PATENT DOCUMENTS

| | | | |
|---|---|---|---|
| 5,182,707 A | 1/1993 | Cooper et al. | |
| 5,489,414 A * | 2/1996 | Schreiber et al. | 422/64 |
| 5,505,308 A * | 4/1996 | Eikmeier et al. | 206/449 |
| 5,510,266 A * | 4/1996 | Bonner et al. | 436/43 |
| 5,632,410 A * | 5/1997 | Moulton et al. | 221/79 |
| 5,645,798 A * | 7/1997 | Schreiber et al. | 422/58 |
| 5,720,924 A | 2/1998 | Eikmeier et al. | |
| 5,783,244 A * | 7/1998 | Vlas et al. | 426/536 |
| 5,810,199 A * | 9/1998 | Charlton et al. | 221/31 |
| 5,854,074 A * | 12/1998 | Charlton et al. | 436/46 |
| 6,475,436 B1 | 11/2002 | Schabbach et al. | |
| 7,597,853 B2 * | 10/2009 | West et al. | 422/102 |
| 2002/0164805 A1 | 11/2002 | Gaa et al. | |
| 2003/0039584 A1 | 2/2003 | Schabbach et al. | |

FOREIGN PATENT DOCUMENTS

| | | |
|---|---|---|
| CA | 2269442 A1 | 10/1999 |
| DE | 10138661 A1 | 5/2002 |
| EP | 0738666 A2 | 10/1996 |
| EP | 0951939 A2 | 10/1999 |
| EP | 1022565 A2 | 7/2000 |

* cited by examiner

*Primary Examiner*—Walter D Griffin
*Assistant Examiner*—Christine T Mui
(74) *Attorney, Agent, or Firm*—Barnes & Thornburg LLP

(57) ABSTRACT

The invention generally relates to a dispensing container for analytical disposables. In particular test elements, for the storage and removal of one disposable each from a storage container provided in the form of a drum cartridge.

29 Claims, 7 Drawing Sheets

DISPENSING CONTAINER AND STORAGE CONTAINER FOR ANALYTICAL DISPOSABLES

REFERENCE TO RELATED APPLICATIONS

The present application claims priority to German Patent Application No. 10353445.8, filed Nov. 15, 2003, which are hereby incorporated by reference in their entirety:

TECHNICAL FIELD

The invention generally relates to a dispensing container for analytical disposables. In particular to a dispensing container for test elements and for the storage and removal of one analytical disposable each from a storage container.

BACKGROUND

Rapid tests on a carrier test strip have become standard for chemical and biochemical analysis of solid and liquid samples not only in specialized laboratories, but also, in particular, for the use outside of laboratories. Based on a special-developed dry chemistry, these carrier-based rapid tests can be performed easily and without complications even by untrained individuals despite the often complex reactions involving sensitive reagents. The most prominent example of carrier-bound rapid tests are test strips for the determination of the blood glucose level in diabetics. Also well-known are single- or multiple-field test strips for urine analysis and various indicator papers. Since carrier-bound rapid tests also exist in a variety of shapes other than strips (test strips), the term, "analytical test element", is generally used.

Like other analytical disposables, e.g. cuvettes, pipettes or lancets, test strips or test elements of this type need to be protected from dirt, germs and dust by means of a package.

In cases, where the analytical disposables are not directly fed from the storage container to a measuring device, but rather are evaluated by visual inspection with the naked eye, such as e.g. a test strip with an indicator paper, it is important that the analytical disposables can be removed from the storage container as easily as possible and without getting damaged or contaminated in the process. In particular, it is important that the removal is as easy as possible to perform by senior or ill people whose dexterity may be impaired.

SUMMARY

It is therefore an object of the invention to provide a means of protecting analytical disposables in a storage container from dirt, germs and dust while allowing them to be removed as easily as possible from the storage container when needed. In addition, the invention should provide for only one analytical disposable each to be removed at a time and for the analytical disposables contained in the storage container to be removed and consumed successively without individual analytical disposables being missed or remaining unused.

A storage container is inserted into the dispensing container according to the invention, which storage container comprises transport elements acting in concert with the removal facility of the dispensing container to move the storage container inserted into the dispensing container for the removal of the disposable to be removed next.

It is advantageous in a dispensing container according to the invention to have a movement of the lid actuate the removal facility such that a disposable is automatically pushed from a chamber of the storage container when the lid is being opened, and can then be grasped by the user of the dispensing container. In addition, upon opening or preferably upon closing of the lid, the storage container is advanced to a position such that the disposable to be removed next is automatically pushed from the next chamber when the lid is being opened next.

In order to remove an analytical disposable from a dispensing container according to the invention with a storage container according to the invention, it is sufficient to open the lid of the dispensing container. As a consequence, it is relatively easy to remove disposables from the storage container and the disposables do not get contaminated or damaged while being removed due to inexpert contact. Moreover, there is no need to search for or find the next analytical disposable to be removed, since it is provided automatically by the dispensing container.

In addition, it is advantageous to be able to remove from the dispensing container a storage container, from which all disposables have been removed, and replace it by a storage container filled with disposables such that the dispensing container can be reused a virtually unlimited number of times, whereas the storage container can be a disposable article.

BRIEF DESCRIPTION OF THE DRAWINGS

The following detailed description of the embodiments of the present invention can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figure may be exaggerated relative to other elements to help improve understanding of the embodiment(s) of the present invention.

DETAILED DESCRIPTION

The following description of the preferred embodiment is merely exemplary in nature and is in no way intended to limit the invention or its application or uses.

Figure 1:
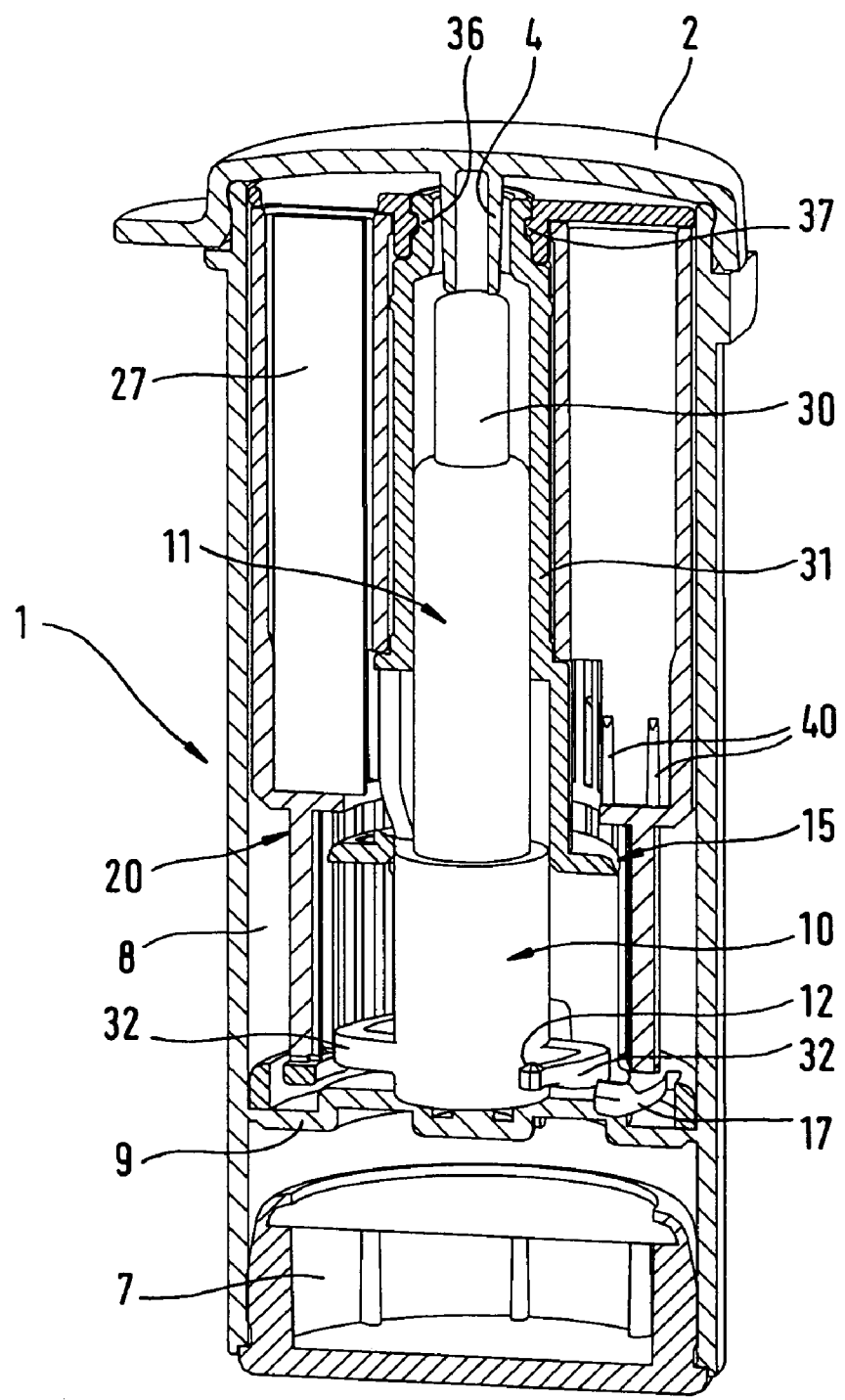
FIG. 1 shows a cross-section of an embodiment with the lid being closed.
Figure 2:
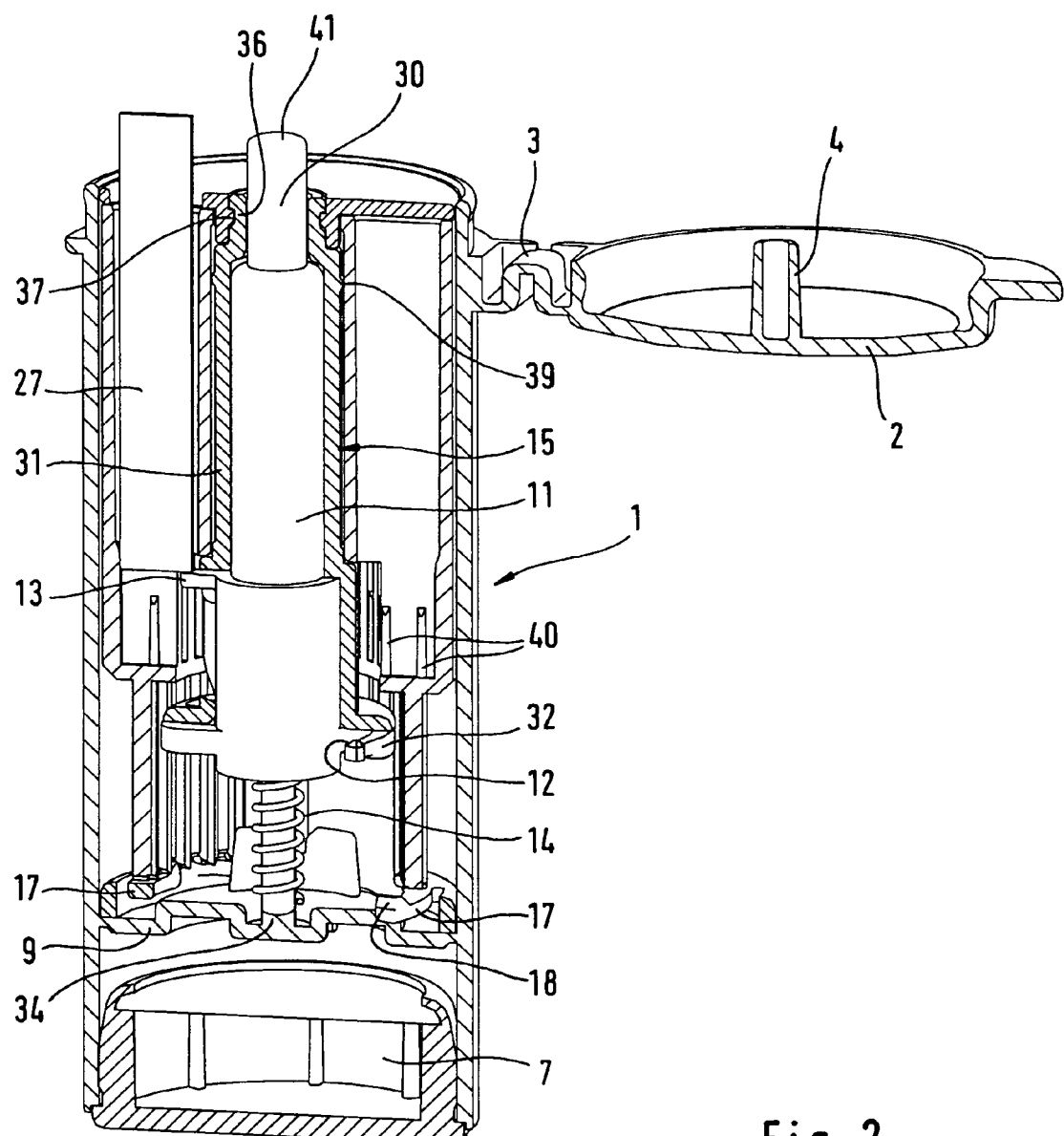
FIG. 2 shows the embodiment shown in FIG. 1 with the lid being open.

FIG. 1 shows a cross-section of an embodiment of a dispensing container 1, in which a storage container-receiving chamber 8 contains a storage container 20 containing analytical disposables 27 in the form of test strips, with the lid 2 being closed. The dispensing container 1 and the lid 2 are provided in the form of one part. It is preferable that eh storage container 20 dispensing container 1 and lid 2 are made of a rigid material, e.g. as an injection molded part made from polyethylene or polycarbonate. FIG. 2 also shows a cross-section of the embodiment shown in FIG. 1 with the lid 2 being open. The dispensing container 1 is essentially cylinder-shaped and one of its front surfaces can be closed by means of the round lid 2 which is attached by means of a joint 3. Here, joint 3 is formed by a flexible fin connecting the lid 2 to the dispensing container 1 such that it is capable of pivoting.

Referring in particular to FIG. 1, the dispensing container 1 has a base 9 on which rests a removal means 10. The removal means 10 is explained in more detail below and shown in FIGS. 3 and 5. The removal means 10 supports the storage container 20 as shown in detail in FIGS. 4 and 6, which contains the disposables 27. The removal means also advances the storage container 20 to a changed position for the removal of the next disposable 27 upon closure of the lid 2.

Figure 4:
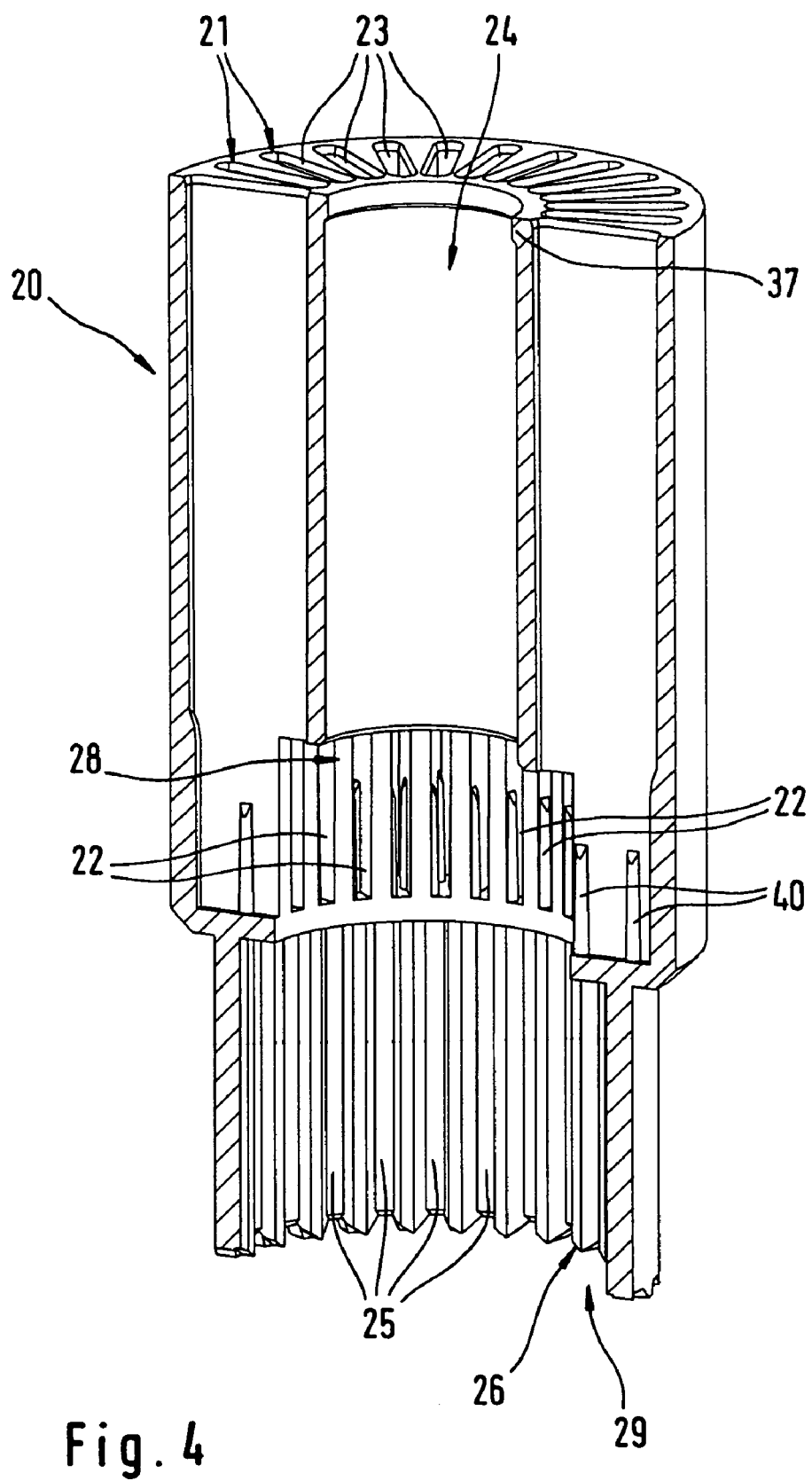
FIG. 4 shows a cross-section of an embodiment of a storage container.

The storage container 20, shown in particular in FIG. 4, is provided in the shape of an essentially cylindrical drum cartridge and is rotationally symmetrical about its longitudinal axis. The storage container 20 comprises transport elements 25, 26, which are illustrated in more detail in the following and are shown in particular in FIG. 6 and act in concert with the removal facility 10 to move the storage container 20, which is inserted into the dispensing container, for the removal of the next disposable 27. The storage container 20 comprises an elongated hole 24, which is a through-hole in longitudinal direction and in the center of which extends the geometrical axis of rotation of the storage container 20. The actuation part 11 is arranged inside the elongated hole 24 of the storage container, through which the rotation axis extends, as shown in FIGS. 1 and 2.

Chambers 21 for the analytical disposables 27, which are provided in the form of test strips, are arranged in a geometrically regular arrangement around the elongated hole 24. Each chamber 21 contains a holder 40 fixing the disposable 27 that is stored in the respective chamber 21.

In the embodiment shown, 25 chambers 21 are provided, but their number can be selected freely within wide limits. For most applications, it is useful to provide 10 to 100 chambers, preferably 15 to 50, particular preferable 20 to 30 chambers 21. The drum cartridge comprises geometric subdivisions which match the number of chambers 21 and determine an incremental rotation step for the removal of a next disposable 27. The chambers 21 each exit into a removal opening 23 at a front surface of the storage container 20. An insertion opening 22 in the shape of a slit extending in longitudinal direction is provided for each of the chambers 21 in the internal side wall 28 of the storage container 20 facing the elongated hole 24.

As will be explained in more detail in the following, a disposables driver 13 of the removal facility 10 can engage the removal openings 23 and push the analytical disposable 27 through the removal opening 23 from the respective chamber 21.

In the exemplary embodiment shown, the length of the slit-shaped insertion opening 22 defines the path along which the disposables driver 13 pushes the analytical disposable 27 forward and therefore also defines how far the analytical disposable 27 protrudes when the dispensing container 1 is in the open position shown in FIG. 2. For most analytical disposables, in particular test strips, one end of the disposable 27 should protrude approx. 4 to 20 mm, preferably approx. 4.5 to 10 mm, when the dispensing container 1 is in the open position shown in FIG. 2. If the disposable 27 protrudes less far, it may be difficult to grasp; if it protrudes even farther, there is an increasing risk of it inadvertently falling from its chamber 21 or being damaged or contaminated. It is self-evident that in individual cases of specific analytical disposables a different length of the slit-shaped insertion opening 22 and therefore a different length of protrusion of the disposable 27 from the dispensing container 1 may be adequate.

The insertion openings 22 and the removal openings 23 are sealed by foil (not shown) in order to protect the analytical disposables 27 from detrimental environmental influences, such as dust, moisture or light. In order to remove a disposable 27, the foil of the insertion opening 22 is punctured by the disposables driver 13 of the removal facility 10 shown especially in FIGS. 3 and 5, and the foil of the removal opening 23 is punctured by the analytical disposable 27 itself. The foil preferably consists of plastic or aluminum, but can as well consist of any other suitable material, such as for instance coated paper.

Figure 3:
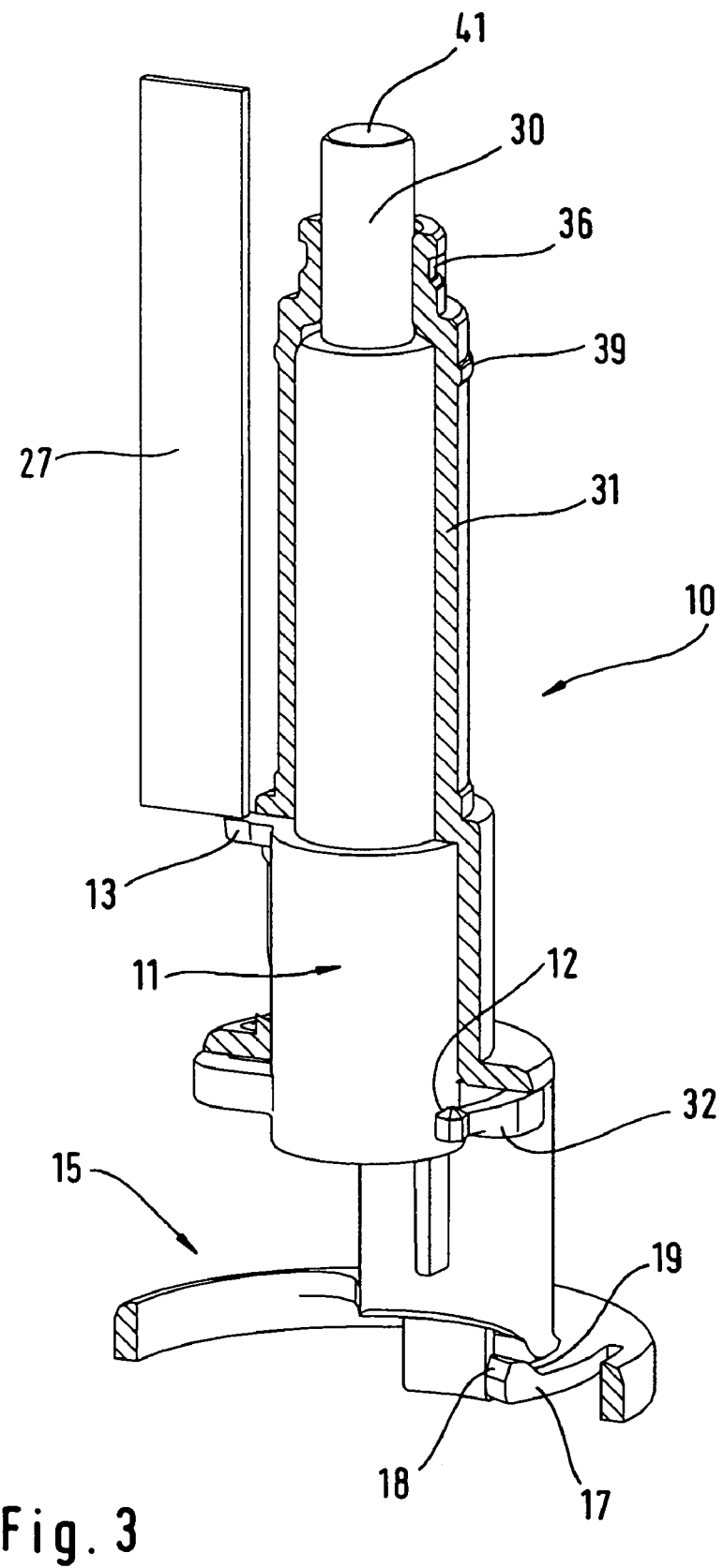
FIG. 3 shows a side view of the removal facility of the embodiment.
Figure 5:
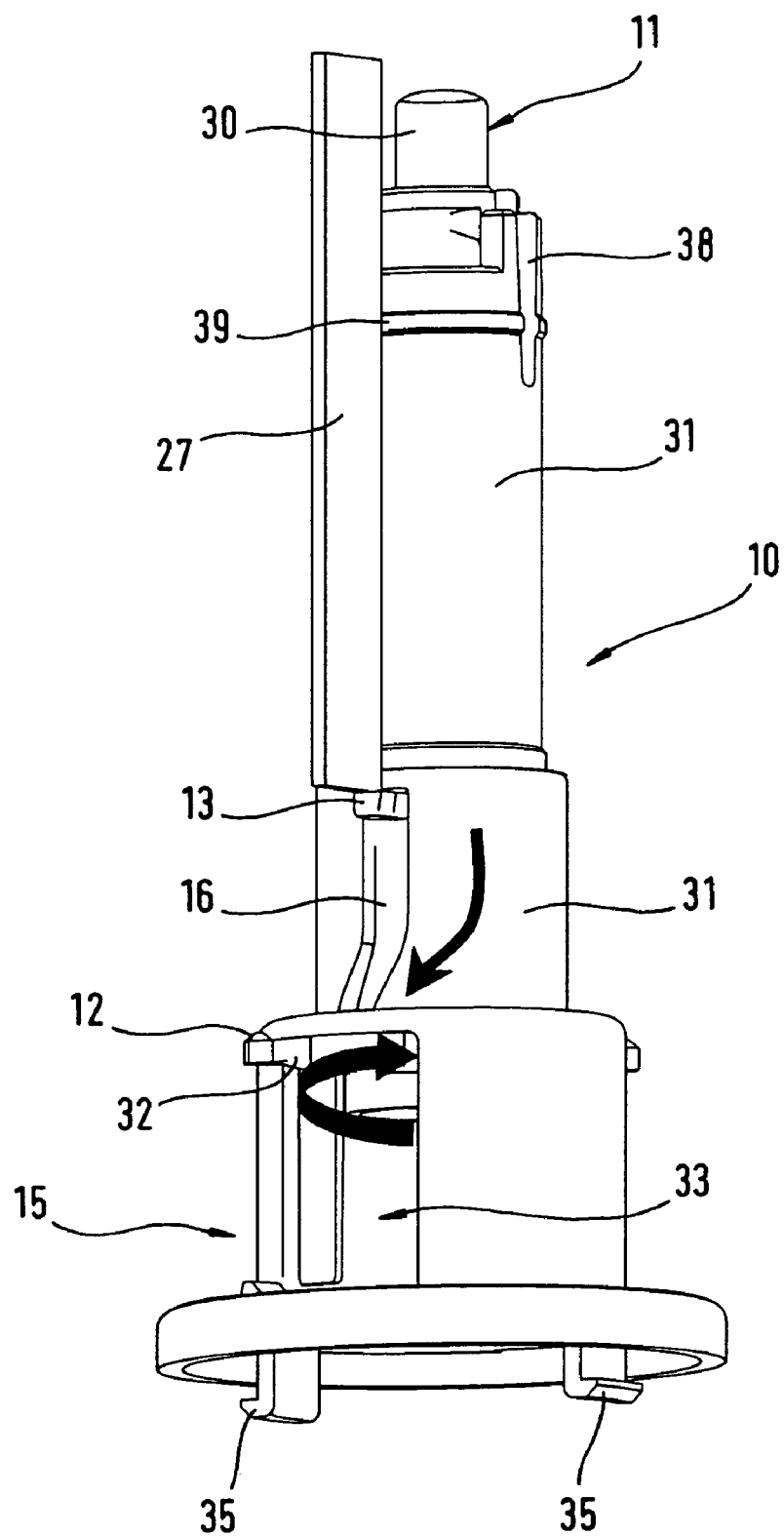
FIG. 5 shows another view of the embodiment shown in FIG. 3.
Figure 6:
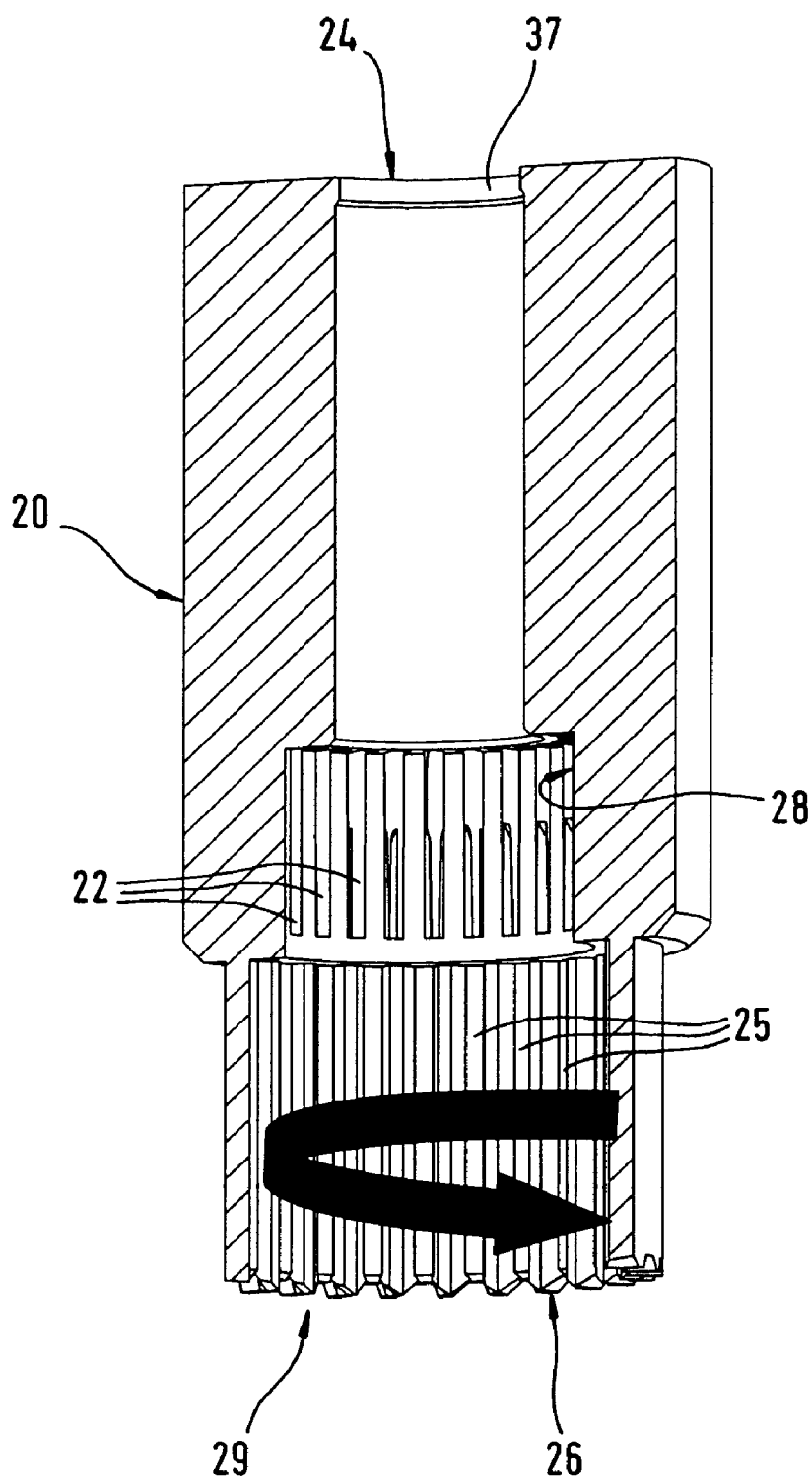
FIG. 6 shows another view of the embodiment shown in FIG. 4.
Figure 7:
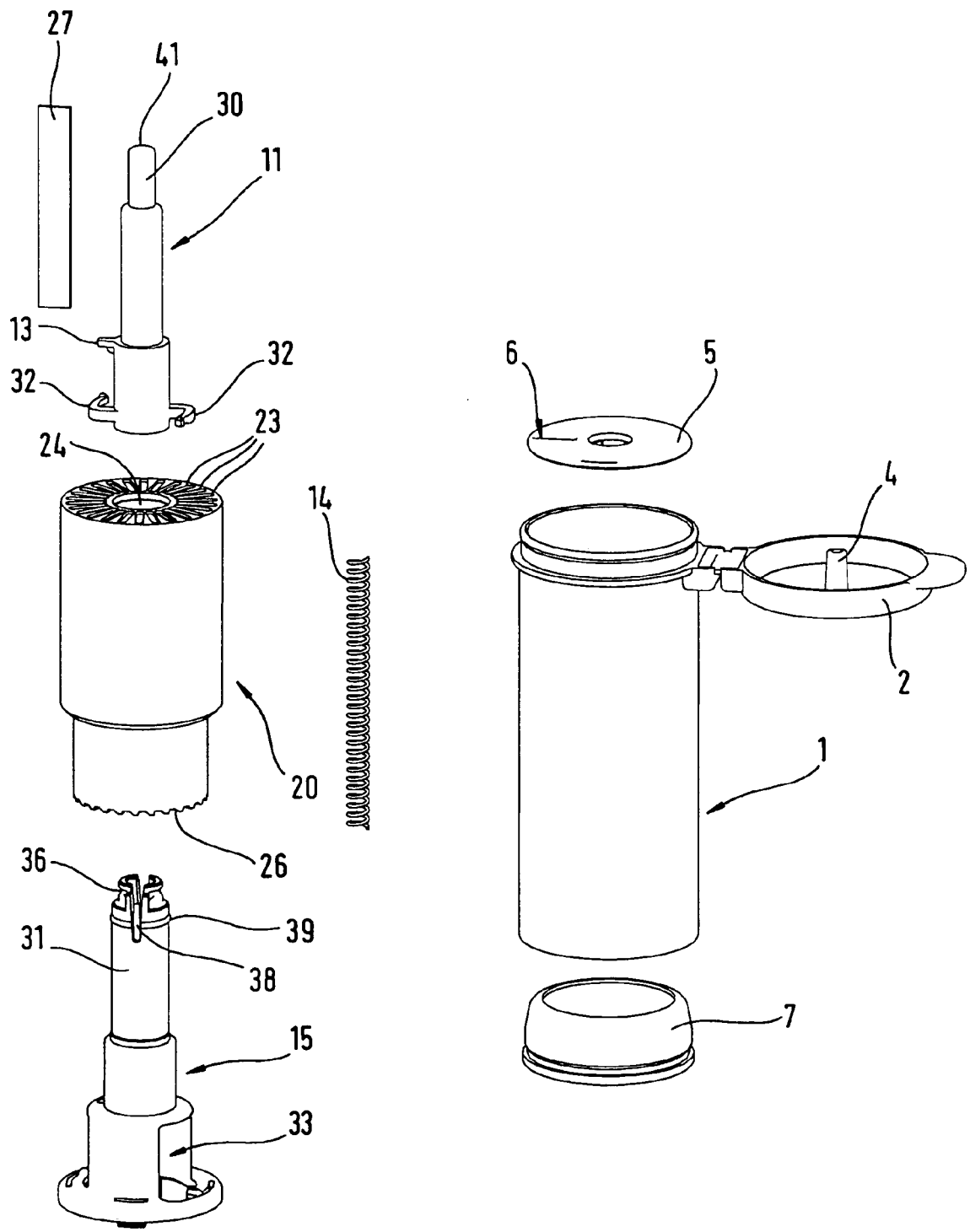
FIG. 7 shows various details of the embodiment.

The removal facility 10 shown in FIGS. 3 and 5 comprises an actuation part 11, a support 15 for the storage container 20, and a spring 14 as is particularly evident from FIG. 7. The removal facility 10 is provided such that it advances the storage container 20 by rotating the storage container about its longitudinal axis into the position for the removal of the next disposable.

In order to convey and convert the movement of the actuated lid 2 upon opening or closing of the lid 2 into an advancement of the storage container 20 to a changed position, the removal facility 10 comprises an actuation part 11, which is capable of moving inside the dispensing container 1 and is pushed against a spring 14 shown in FIG. 2 in a direction towards the inside of the dispensing container 1 when the lid 2 is closed, and is pushed by spring 14 in a direction out of the dispensing container 1 when the lid 2 is opened, whereby the storage container 20 is advanced by moving the actuation part 11.

A projection 4 projecting towards the inside of the dispensing container 1 is attached or arranged on lid 2 and pushes against the spring 14 in a direction towards the inside of the dispensing container 1 when the lid 2 is closed onto the actuation part 11. This projection 4 is arranged in the middle of the lid 2.

Like the support 15, the actuation part 11 is provided in the form of a single-part injection molded part. The actuation part 11 comprises a driver pin 30 which is capable of moving in longitudinal direction within a support sleeve 31 of the support 15. Upon closing of the lid 2, the driver pin 30 is pushed downwards in the support sleeve 31 by the projection 4 of the lid 2, as is evident from FIGS. 1 and 2, whereby a spring 14 is compressed.

The spring 14 is a helical compression spring, which surrounds a positioning pin 34 which is attached to the base 9, as shown in FIG. 2. Upon opening of the lid 2, the spring 14 pushes the driver pin 30 of the actuation part 11 upwards such that the disposables driver 13, which is rigidly connected to the driver pin 30, pushes an analytical disposable 27 from its chamber 21.

The support 15 supports the storage container 20 and acts in concert with the actuation part 11 of the removal facility 10 such that, upon closing of the lid 2 of the dispensing container 1, the storage container 20 is automatically advanced by one subdivision of the regular geometric arrangement of the chambers 21 such that another disposable 27 can be removed from the next chamber 21 when the lid 2 is opened again.

As is best seen in FIG. 3, the actuation part 11 comprises a disposables driver 13, which extends as a pin-like projection perpendicular to the direction of motion of the actuation part 11 through one of the insertion openings 22 into one of the chambers 21. The disposables driver 13 not only serves the function of pushing a disposable 27 from a chamber 21 for the removal of the disposable, but also effects a rotation of the storage container 20 by one incremental rotation step, the size of which depends on the number of chambers 21, when the actuation part 11 is pushed down, as occurs in particular when the lid 2 is closed.

In order to convert the longitudinal movement of the actuation part 11, especially of the driver pin 30, into a rotational movement, the disposables driver 13 is guided in a guiding slit 16 of the support 15, which is shown in FIG. 5. In its front part facing the dispensing opening, the guiding slit 16 is straight and guides the disposables driver 13 along one of the slit-shaped insertion openings 22 of one of the chambers 21 of the storage container 20 such that a disposable 27 is pushed out. In its rear part, the guiding slit is curved and extends just far enough in the direction of the circumference for the disposables driver 30 to be guided relative to the support sleeve 31 during an incremental rotation step by the distance between one chamber 21 and the neighboring chamber 21. Presuming exactly 25 chambers 21 to be provided in the storage container 20 as in the embodiment shown, the beginning and the end of the guiding slit 16 are offset from each other in the direction of rotation of the storage container 20 by ¹/₂₅ of the circumference of the support sleeve 31.

Accordingly, moving the disposables driver 13 along the guiding slit 16 rotates the entire actuation part 11 relative to the support 15 by one subdivision of the regular geometrical arrangement. Moreover, the support 15 also locks the actuation part 11 in a position for the removal of one of the disposables 27 by means of the guiding slit 16.

In addition, the actuation part 11 comprises two rigid guiding arms 32, which each reach through one recess 33 of the support 15. In general, one guiding arm 32 is sufficient to perform the functions described in the following, but providing two radial-opposite guiding arms 32 enhances the mechanical reliability of the removal facility 10.

The two guiding arms 32 each comprise a head with a propulsion element 12 at their free end. The propulsion element 12 engages one of the grooves 25 of the storage container 20 which extend in longitudinal direction. These grooves 25 are part of the earlier mentioned transport elements of the storage container 20, which serve to move the storage container 20. The propulsion elements 12 can move in longitudinal direction inside these grooves 25 when the removal facility 10 is actuated, i.e. upon opening and closing of the lid 2.

An incremental rotation step of the actuation part 11 is conveyed by the guiding arm 32 and the propulsion element 12 to the storage container 20 via the groove 25 of the storage container 20 that is engaged by the propulsion element 12.

This way, each time the lid 2 of the dispensing container 1 is opened, the removal facility 10 pushes a disposable 27 from its respective chamber 21, whereas each time the lid 2 is closed, the storage container 20 and the actuation part 11 are jointly rotated by another incremental rotation step such that another disposable 27 is pushed from the neighboring (in the direction of the circumference) chamber 21 when the lid 2 is opened next. The guiding arms 32 therefore fix the storage container 20 relative to the actuation part 11 by the propulsion elements 12 acting in concert with the grooves 25 of the storage container 20. Therefore, when the lid 2 is actuated, the storage container 20 is advanced by one subdivision of the geometrical arrangement.

The removal facility 10 comprises positioning elements 17 for locking the storage container 20 in a position of the regular geometrical arrangement. In order to prevent an undesirable backwards rotation of the storage container 20, these positioning elements comprise retaining clips 17 shown in FIG. 3, which are arranged on the support 15 and engage a toothed ring 26 of the storage container 20, which also is part of the earlier-mentioned transport elements of the storage container 20. As shown in FIG. 3, the retaining clips 17 comprise a locking surface 18 and a gliding surface 19, with the latter being arranged opposite to the former in the direction of the circumference of the dispensing container 1.

The gliding surface 19 is inclined with respect to the direction of rotation such that the toothed ring 26 of the storage container 20 can glide over the gliding surface 19 during a rotational movement and thus perform an incremental rotation step. The opposite locking surface 18 is much more inclined than the gliding surface 19 or even provided to be perpendicular such that the toothed ring 26 cannot or only with difficulty glide over the locking surface 18 and thereby the storage container 20 is prevented from rotating backwards by the incremental rotation step just performed. The retaining clips 17 and the toothed ring 26 thus act as positioning elements locking the storage container 20 in a suitable position for the removal of a disposable 27.

As is shown in FIG. 5, the support 15 comprises snap-in feet 35 fixing it secured against twisting to the base 9 of the dispensing container 1. The support sleeve 31 comprises a spacer 39 in the shape of an annular ring to simplify the insertion of the support sleeve 31 into the elongated hole 24 of the storage container 20 and still achieve good axial positioning. The spacer maintains a small distance between the support sleeve 31 and the storage container 20 such that the insertion is not associated with excessive frictional forces.

In order to further support the correct positioning of the storage container 20 relative to the support 15, the support 15 can be locked to the storage container 20. For this purpose, the support sleeve 31 comprises snap-in elements 36 which engage the snap-in elements 37 of the storage container 20. In the exemplary embodiment shown, the snap-in elements 36 of the support sleeve 31 are provided as a continuous annular groove at or near the front surface of the support sleeve 31 facing the lid 2. The snap-in elements 37 of the storage container 20 are provided as a matching annular ring inside the elongated hole 24. To simplify the locking of the snap-in elements 36, 37, the support sleeve 31 is provided with a longitudinal slit 38 in the area of the snap-in elements 36 rendering it somewhat compressible in this area.

To support the axial positioning, the driver pin 30 comprises a rounded surface 41, which acts in concert with the hollow projection 4 of the lid 2. When the projection 4 pushes against the rounded surface 41 of the driver pin 30, it causes the driver pin to positioned itself such that it is in a concentric alignment with respect to the projection 4.

The dispensing container 1 comprises a replaceable desiccant insert 7, which also serves to seal the dispensing container 1 at its front surface opposite to the lid 2. Alternatively or in addition, a desiccant can be provided also inside the storage container 20, for example in each of the chambers 21.

As is shown in FIG. 7, the dispensing container 1 comprises a transparent cover 5, which covers the inserted storage container 20 and comprises a dispensing opening 6, below which one removal opening 23 of the chambers 21 of the storage container 20 each is positioned for the removal of a disposable 27 from the inserted storage container 20 by means of the removal facility 10. Inside the dispensing container 1, the cover 5 protects the storage container 20 and in particular the foil sealing the removal openings 23 from undesirable damage. The cover 5 is transparent to allow a user of the dispensing container 1 to easily see how many test elements 27 are left in the storage container 20.

Once all disposables 27 have been removed from the storage container 20, the storage container 20 can be replaced by a new, filled storage container 20 or the dispensing container can be disposed of together with the empty storage container 20. It is preferable for the storage containers 20 to be capable of being refilled, but they can as well be disposable items.

If the dispensing container 1 is designed for multiple use, i.e. if it is intended to replace a storage container 20 once it is empty with a new, filled storage container 20, it is preferable for the insertion openings 22 and the removal openings 23 of the storage container 20 to be sealed air-tight by foil. In this case, it is preferable to have a desiccant in each of the chambers 21 such that a replaceable desiccant insert 7 for the dispensing container 1 is superfluous allowing the dispensing container 1 to be designed somewhat more compact in shape.

If the dispensing container 1 is designed to be a disposable item to be disposed of together with an empty storage container 20, the air-tight storage of the disposables 27 stored in the storage container 20 can be achieved without sealing the insertion openings 22 and removal openings 23. The two front surfaces of the dispensing container 1 each can be sealed air-tight by means of the lid 2 and the desiccant insert 7. In this case, the cover 5 protects the disposables 27 stored in the chambers 21 when the lid 2 is open.

Having described the invention in detail and by reference to specific embodiments thereof, it will be apparent that modification and variations are possible without departing from the scope of the invention defined in the appended claims. More specifically, although some aspects of the present invention are identified herein as preferred or particularly advantageous, it is contemplated that the present invention is not necessarily limed to these preferred aspects of the invention.

These and other features and advantages of the present invention should be more fully understood from the above detailed description of the invention taken together with the accompanying claims. It is noted that the scope of the claims is definitely by the recitations therein and not by the specific discussion of the features and advantages set forth in the present description.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may very from a stated reference without resulting in a change in the basic function of the subject matter at issue.

What is claimed is:

1. A dispensing container for storage and removal of analytical disposables, the dispensing container comprising:
    a storage container comprising multiple chambers configured to sealably store one analytical disposable in each, wherein the chambers are in a regular geometric arrangement with respect to each other and wherein each chamber comprises at least first and second openings, the first opening comprising an insertion opening configured for insertion of a driver, the second opening comprising a removal opening through which removal of the analytical disposable from the chamber is achieved;
    a storage container-receiving chamber for receiving the storage container;
    a lid for sealably closing the storage container-receiving chamber; and
    a removal means configured to be actuated by movement of the lid for the removal of analytical disposables from the storage container;
wherein upon movement of the lid the removal means advances the storage container to a position for the removal of a next analytical disposable, and
wherein the removal means is operatively connected to the driver and is configured to cause the driver to push the analytical disposable at least partly from its chamber through the removal opening upon opening of the lid such that the analytical disposable can be grasped by a user.

2. The dispensing container according to claim 1, wherein the storage container is advanced upon each actuation of the lid by one subdivision of the regular geometric arrangement.

3. The dispensing container according to claim 1, wherein the removal means advances the storage container to a position for the removal of the next disposable when the lid is closed.

4. The dispensing container according to claim 1, wherein the lid is attached to the dispensing container by means of a joint such that it is capable of pivoting.

5. The dispensing container according to claim 1, wherein the removal means comprises an actuation part, which is capable of moving inside the dispensing container and is pushed against a spring in a direction towards the inside of the dispensing container when the lid is closed, and is pushed by the spring in a direction out of the dispensing container when the lid is opened, whereby the storage container is advanced by moving the actuation part of the removal means.

6. The dispensing container according to claim 5, wherein a projection is positioned on the lid such that the projection pushes against the spring in a direction towards the inside of the dispensing container when the lid is closed.

7. The dispensing container according to claim 6, wherein the projection is positioned in the middle of the lid.

8. The dispensing container according to claim 1, wherein the dispensing container and the storage container are cylindrical in shape and in that the regular geometric arrangement is a rotation-symmetrical arrangement of the chambers of the storage container about a longitudinal axis of the storage container.

9. The dispensing container according to claim 5, wherein the actuation part is arranged in an elongated hole of the storage container.

10. The dispensing container according to claim 1, wherein the storage container has a regular geometric arrangement with from about 10 to about 100 subdivisions.

11. The dispensing container according to claim 1, wherein the lid is round and seals the dispensing container on one of its front surfaces.

12. The dispensing container according to claim 1, wherein the removal means advances the storage container into the position for the removal of the next analytical disposable by rotating the storage container about its longitudinal axis.

13. The dispensing container according to claim 1, wherein the removal means comprises positioning elements for locking the storage container in a position for removal of the analytical disposable.

14. The dispensing container according to claim 13, wherein the positioning elements comprise retaining clips for engaging the storage container.

15. The dispensing container according to claim 14, wherein the retaining clips comprise a locking surface and a gliding surface, wherein the guiding surface is arranged opposite to the locking surface in the direction of the circumference of the dispensing container, whereby the gliding surface is inclined with respect to the rotation axis of the storage container.

16. The dispensing container according to claim 1, further comprising a cover to cover the storage container, wherein the cover has an opening such that it is above the removal opening of a chamber of the storage container.

17. The dispensing container according to claim 16, wherein the cover is transparent.

18. The dispensing container according to claim 1, wherein the storage container inserted into the dispensing container is replaceable.

19. The dispensing container claim 5, wherein the removal means further comprises a support means for the storage container.

20. The dispensing container according to claim 19, wherein the support means locks the actuation part in place.

21. The dispensing container according to claim 19, wherein the support means comprises a support sleeve, in which a driver pin of the actuation part can move.

22. The dispensing container according claim 5, wherein the storage container can be fixed in place relative to the actuation part and the actuation part is advanced by the removal means of the dispensing container for the removal of the next disposable.

23. The dispensing container according to claim 1, wherein the storage container inserted into the dispensing container can be refilled with the analytical disposables.

24. The dispensing container according to claim 1, wherein the chambers of the storage container are each sealed by foil, which is punctured by the driver during the removal of the analytical disposable.

25. The dispensing container according to claim 1, wherein a desiccant insert is inserted in the dispensing container on the front end of the dispensing container opposite from the lid.

26. The dispensing container according to claim 1, wherein the removal means pushes the analytical disposable with the driver from its chamber to the extent that an end of the analytical disposable that can be grasped by the user protrudes from the removal opening by about 4 to about 20 mm for grasping.

27. The dispensing container according to claim 26, wherein the end of the analytical disposable protrudes from the removal opening by about 4.5 to about 10 mm for grasping.

28. The dispensing container according to claim 10, wherein the regular geometric arrangement comprises from about 15 to about 50 subdivisions.

29. The dispensing container according to claim 28, wherein the regular geometric arrangement comprises from about 20 to about 30 subdivisions.

* * * * *